United States Patent [19]
Townsend

[11] Patent Number: 4,890,607
[45] Date of Patent: Jan. 2, 1990

[54] MULTIAXIS CONTROLLED MOTION KNEE ORTHOSIS

[76] Inventor: Jeffrey H. Townsend, 7106 Crestwood St., Bakersfield, Calif. 93308

[21] Appl. No.: 250,068

[22] Filed: Sep. 28, 1988

[51] Int. Cl.$^4$ ................................................ A61F 3/00
[52] U.S. Cl. ..................................... 128/80 C; 128/88
[58] Field of Search ...................... 128/80 C, 80 F, 88, 128/165

[56] References Cited

U.S. PATENT DOCUMENTS

| | | | |
|---|---|---|---|
| 552,143 | 12/1895 | Rankin | 128/80 F |
| 1,390,915 | 9/1921 | Loth | 128/80 F |
| 3,552,786 | 1/1971 | Schmid | 128/80 F |
| 3,779,654 | 12/1973 | Horne | 128/80 C |
| 3,826,251 | 7/1974 | Ross | 128/80 F |
| 3,902,482 | 9/1975 | Taylor | 128/80 F |
| 4,088,130 | 5/1978 | Applegate | 128/80 F |
| 4,340,041 | 7/1982 | Frank | 128/88 |
| 4,353,361 | 10/1982 | Foster | 128/88 |
| 4,506,661 | 3/1985 | Foster | 128/80 C |
| 4,554,913 | 11/1985 | Womack et al. | 128/88 |
| 4,603,690 | 8/1986 | Skeen | 128/80 |
| 4,723,539 | 2/1988 | Townsend | 128/80 C |
| 4,726,361 | 2/1988 | Farley | 128/80 F |

FOREIGN PATENT DOCUMENTS 2600528 12/1987 France ............................. 128/80 C

*Primary Examiner*—Edgar S. Burr
*Assistant Examiner*—Huong Q. Pham
*Attorney, Agent, or Firm*—Sixbey, Friedman, Leedom & Ferguson

[57] ABSTRACT

An improved multiaxis controlled motion knee orthosis in the form of a knee brace appliance wherein a joint mechanism is provided that utilizes two camming slots and cam pin followers to achieve an arthrokinematic movement comprised of an anterior motion of a femoral link relative to a tibial link during an initial phase of flexion followed by a unicentric phase of movement. In accordance with a preferred embodiment, during the initial range of motion, pivoting occurs through a short transverse arc segment about an upper one of the cam pin followers that is disposed within a longitudinally extending arcuate slot forming one of the two camming slots, while the unicentric movement is produced, after a lower one of the cam pin followers reaches the anterior end of a transverse slot forming the other of the two camming slots, the lower cam pin follower serves as the axis of rotation or pivot point for movement of the upper cam pin follower along the longitudinally extending arcuate slot. Additionally, an internal range of motion limiter comprised of one or more pins that can be selectively interconnected between the femoral link and a joint cover plate provide a selective control of extension and/or flexion over a wide range. Furthermore, a femoral cuff is provided that is comprised of a pair of side wings interconnected, solely at an upper end thereof, by a narrow bridge, thereby giving the cuff a generally n-shaped appearance and providing increased comfort for the wearer.

20 Claims, 3 Drawing Sheets

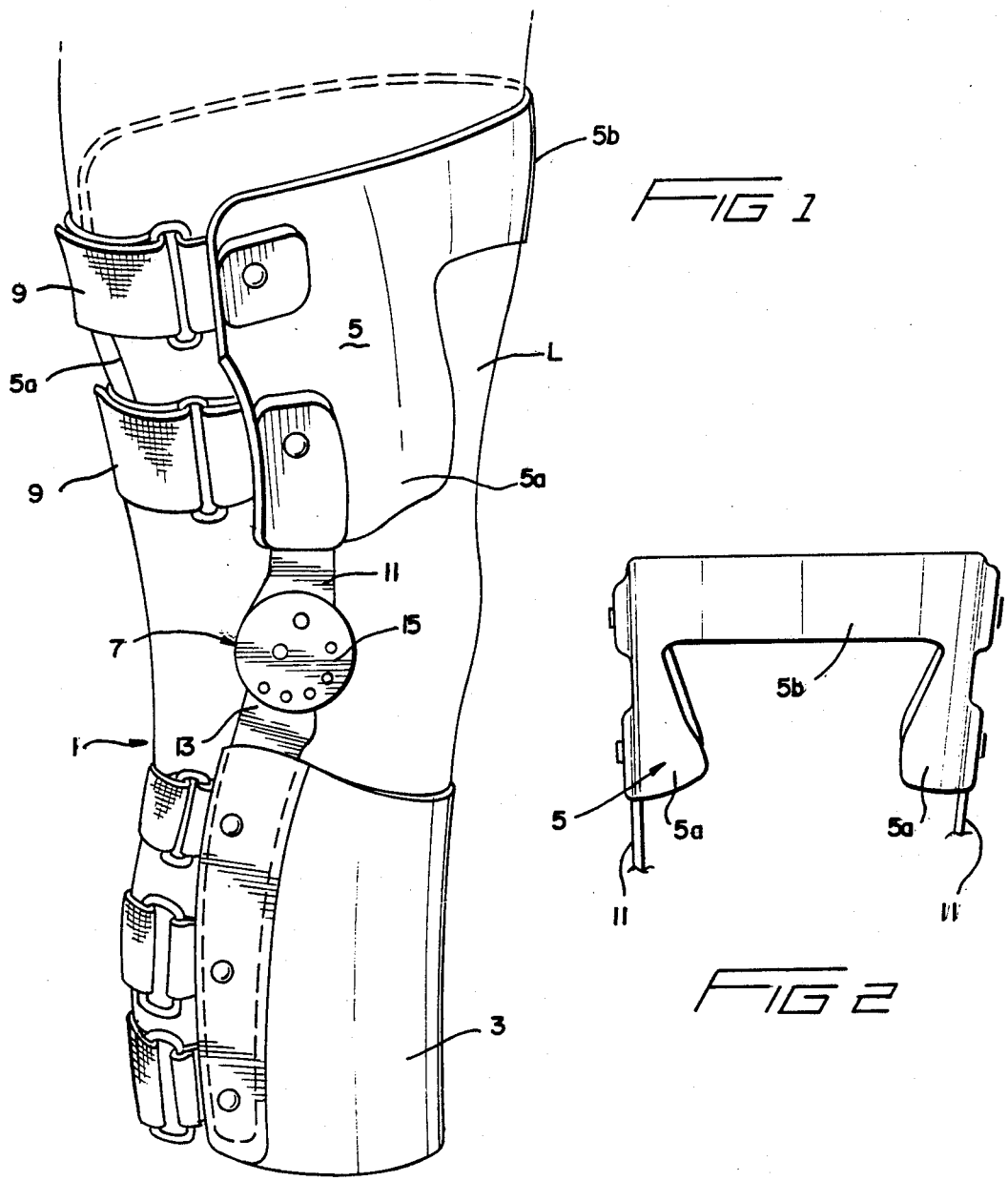

MULTIAXIS CONTROLLED MOTION KNEE ORTHOSIS

BACKGROUND OF THE INVENTION

1. Field of the Invention

The present invention relates to orthopedic devices for the stabilization and control of a human knee joint which has been injured. More particularly to provide a knee brace which will permit the user a relatively high degree of freedom in the use of the bones while, at the same time, permitting control of the joint so as to optimize healing and stability.

2. Description of Related Art

Devices for adding support and strength to the knee joint have been known for decades and have taken many different forms. While substantially all of these devices have been purported to have mechanical joints designed to produce a smooth articulation of the mechanical joint that is matched to the behavior of the natural human knee joint, very few have, in fact, done so since most known devices have apparently taken for granted that the relative movement of the femur and tibia is a rotation about a single center of rotation, typically in the center of the knee. However, studies have shown that a single pivot movement does not emulate the relative movement of the femur and tibia, and that to do so a mechanical joint must produce an initial rearward movement of the tibia relative to the femur, through the first 25 degrees of flexion, of approximately 8-9 millimeters, followed by a single axis pivot-type rotational movement as the knee continues to flex through a 125° angle, or for whatever angle may be traversed, as limited by the injury or natural limitations of the wearer.

In U.S. Pat. No. 4,603.690 to Skeen, a sliding pivot knee joint is disclosed which produces a rearward sliding of the tibia relative to the femur for a predetermined distance during an initial range of flexion of the knee from a straight leg position and, beyond this initial range of flexion to, thereafter, provide a rotational movement in a path which is a circular segment. However, this sliding pivot knee joint is designed for use by a person whose knee joint has become so weakened or diseased that a collapse may be precipitated by the accidental shifting of the person's weight, while standing, onto the braced leg. As a result, the joint is designed to automatically lock against hyperextension. and also against unintential folding of the knee joint in the direction it normally flexes, in response to the wearer's weight being loaded onto the joint by a shifting of the person's body weight onto the leg wearing the brace. Plainly, such a characteristic would be highly undesirable in a brace intended to protect a healthy or only mildly injured or recuperating knee joint of an athlete participating in active sports, such as football and basketball, where locking of the knee joint at the wrong time could be potentially hazardous.

In Schmid U.S. Pat. No. 3,552,786, the need for a mechanical joint assembly which will prevent hyperextension but which will not lock up so as to prevent normal flexion is recognized. To this end, Schmid discloses a mechanical joint assembly which will produce an initial rearward sliding of the tibia in relation to the femur followed by a rotative movement through an arcuate path wherein a deliberate degree of play is introduced into the joint which is then compensated for by the provision of a displaceable cam member that is biased by an elastomeric compression member housed in a recess of the cam member. While such a joint effectively prevents a lockup of the joint which would make it unsuitable for use, for example, by an athlete, the deliberate introduction of looseness or play into the joint and the reliance upon a resilient elastomeric compression member to take up such play renders the joint unsuitable for the case of a person whose knee joint has degenerated or is otherwise substantially abnormally functioning. That is, in such a case, instead of requiring the knee to produce a proper movement emulating that of a healthy knee joint, such a malfunctioning knee joint is allowed to execute a different and undesirable movement since the biasing effect of the elastomeric compression member may be overcome so as to enable the cam element to shift by an amount corresponding to the extent of the deliberately imposed play or looseness.

In the present inventor's copending U.S. patent application Ser. No. 089,253, filed Aug. 25, 1987, and its parent U.S. Pat. No. 4,723,539, a multiaxis controlled motion knee orthosis is disclosed which is not prone to the shortcomings of either of the above-mentioned patents in that it contains a joint that is designed to constrain the tibia to slide rearwardly relative to the femur for a predetermined distance throughout an initial range of flexion of the knee from a straight leg position, and, beyond that initial range of flexion, to rotate relative thereto along a predetermined arcuate path irrespective of the loading applied to the joint by the leg of the wearer. In the preferred embodiment for a knee joint described in these cases, end portions of femoral and tibial links are interconnected by a cam means comprised of a pair of cam slots formed in the end portion of one of the links and a respective cam follower engaging therein, and wherein each slot has a straight segment adjoining an arcuate segment of equal radius. Such a knee joint has proved excellent in practice and has obtained wide acceptance and utilization. On the other hand, the use of two such slots as disclosed in these preferred embodiments limits the integral strength of the joint, tolerance precision, and production efficiency. Furthermore, an opening disposed in a cover plate element of the joint (for coacting with a post attached to the tibial link for guidance purposes as well as for preventing binding due to frictional forces) can be a source of joint contamination. In another embodiment disclosed in the present inventor's patent and copending Application, provision is made for cases where an orthopedic injury or deformity calls for a restriction in the permissible flexion and/or extension of the knee joint to assure that the user cannot injure himself or herself by either extending or flexing beyond a desirable limit. This is achieved through the use of a motion limiter formed by a modified outside cover plate that has an extension having an arcuate slot opening for an abutment post. However, such a motion limiter, while effective, has proved quite cumbersome.

SUMMARY OF THE INVENTION

In view of the foregoing, it is a primary object of the present invention to provide an improved multiaxis controlled motion knee orthosis which retains the benefits of the inventor's earlier disclosed embodiments while at the same time improving the integral strength of the joint, tolerance precision and production efficiency. More particularly, it is a further object of the present invention to achieve these benefits in a manner which will reduce the potential for joint contamination and enable integration of an internal range of motion limiter into the joint.

In accordance with another aspect of the present invention it is an object to provide a knee brace having a femoral cuff that will firmly hold the upper leg while providing increased comfort relative to a cuff which encircles a major portion of the thigh at top and bottom edges of the cuff.

These and other objects and characteristics of the invention are achieved, in accordance with a preferred embodiment, wherein a joint mechanism is provided that utilizes two camming slots and cam pin followers, in accordance with the biomechanic concepts utilized in the inventor's above-noted cases, but wherein one camming slot is disposed in a transverse plane and serves to provide the anterior motion of the upper joint piece, while the second camming slot is disposed in a longitudinal orientation and provides a long arc segment for the unicentric phase of the joint arthrokinematics. During an initial range of motion, pivoting occurs through a short transverse arc segment about an upper cam pin follower disposed within the longitudinally extending arcuate slot. After the lower cam pin follower reaches the anterior end of the transverse slot, the lower cam pin follower serves as the axis of rotation or pivot point for movement of the upper cam pin follower along the long arc segment of the longitudinal slot. Such an arrangement provides an increase in tolerance precision, full control of the forceful action of the joints throughout the entire range of motion, and by reducing the slot area, increases the integral strength of the joint.

Additionally, the reduction of the area comprised of cam slots allows for a reconfiguring of the tibial link to provide stop surfaces which may be used in conjuction with an internal range of motion limiter comprised of one or more pins that can be selectively interconnected between the femoral link and the joint cover plate to limit, selectively, extension and/or flexion over a wide range.

The femoral cuff is designed so as to be comprised of a pair of side wings interconnected, solely at an upper end area thereof, by a narrow bridge, thereby giving the cuff a generally n-shaped appearance. As a result, the cuff retains the ability to firmly hold the brace upon the upper leg, but without the discomfort that can be associated with a binding of the leg in the lower thigh area.

These and further objects, features, and advantages of the present invention will become more apparent from the following description when taken in connection with the accompanying drawings which show, for purposes of illustration only, a single embodiment in accordance with the present invention.

BRIEF DESCRIPTION OF THE DRAWINGS

FIG. 1 is a side perspective view of an orthosis, in accordance with a preferred embodiment of the invention, shown as mounted on a right leg of a user;

FIG. 2 is a front elevational view of a femoral cuff of the orthosis shown in FIG. 1;

DETAILED DESCRIPTION OF THE PREFERRED EMBODIMENT

Figure 3:
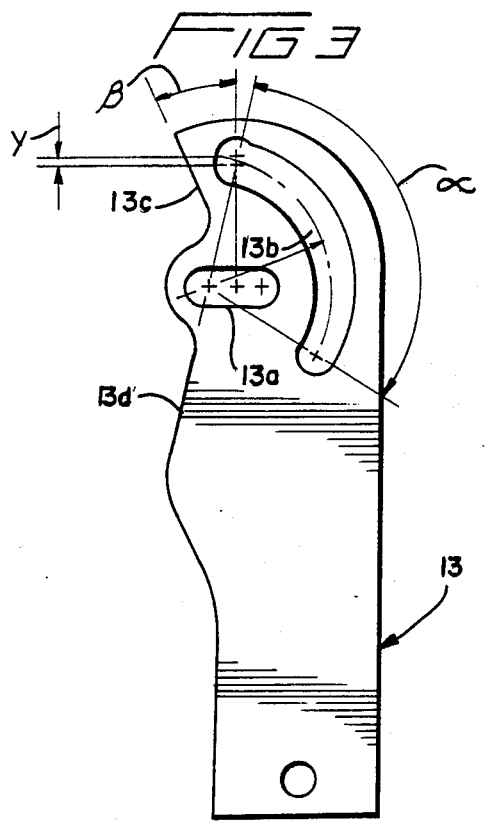
FIG. 3 is a side elevational view of a tibial link of a joint mechanism of the orthosis shown in FIG. 1.
Figure 4:
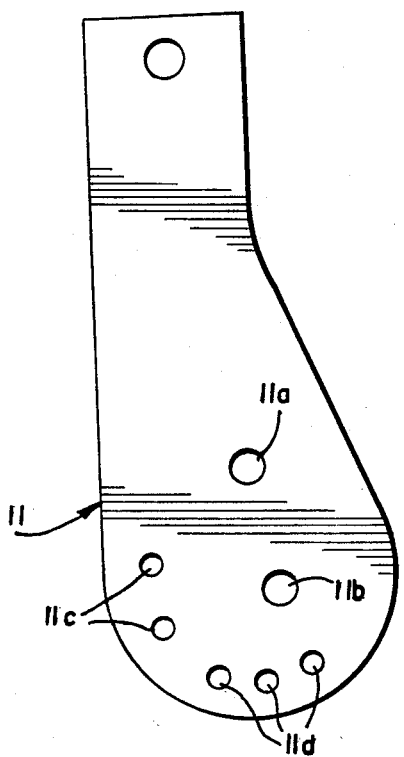
FIG. 4 shows a femoral link of the joint mechanism of the orthosis of the preferred embodiment.
Figure 6:
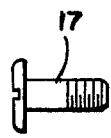
FIG. 6 shows a pin for use as a cam pin, in elevational view.
Figure 5:
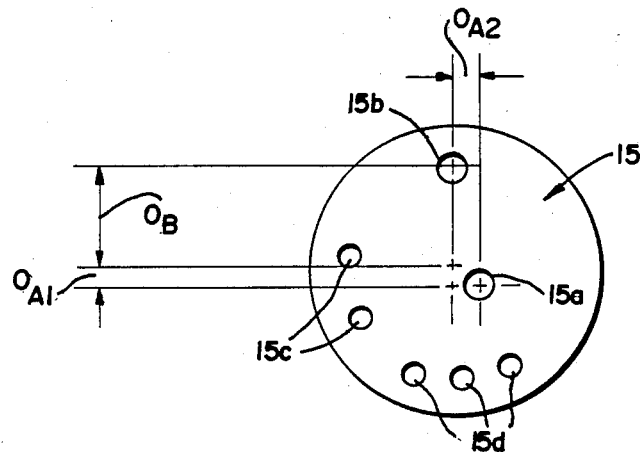
FIG. 5 shows a cover plate of the joint mechanism of the orthosis of FIG. 1.
Figure 7A:
FIGS. 7a, 7b and FIGS. 8a, 8b are plan and elevational views of washers for adjusting the motion limiting effect of the FIG. 6 pin, in accordance with the present invention.
Figure 7B:

At the outset, it is noted that the biomechanics and arthrokinematics of the joint mechanism of the orthosis of the present invention are identical to those disclosed relative to that of the inventor's earlier U.S. Pat. No. 4,723,539 and his copending U.S. patent application Ser. No. 792,770, referred to above. As such, these aspects will not be repeated herein; and to the extent necessary to complete an understanding of the present invention, reference may be had to these earlier cases in these respects. Likewise, the orthosis 1 of the present invention utilizes a tibial cuff 3, that is identical to that disclosed in these earlier cases, so that it too will not be described in detail herein. On the other hand, the femoral cuff 5 and joint mechanism 7 of the orthosis 1 have been modified in significant respects which form the substance of this invention.

The femoral cuff 5, for securing the brace to the thigh of the wearer, is formed of a pair of wings 5a that are interconnected by a bridge portion 5b. Wings 5a are joined together with bridge portion 5b as an integral unit formed of fiberglass or other moldable material that will be custom fit to encircle a major portion of the thigh of a particular user in a manner which will enable it to firmly, but comfortably, be held onto the thigh via a pair of fastening straps 9, in order to secure the upper leg against torsion rotation with respect to the lower leg.

Figure 8A:
Figure 8B:

As can be seen most clearly from FIG. 2, the femoral cuff 5 has an approximately n-shaped appearance, resulting from the removal of material from the cast cuff in a manner which results in significant lightening of the cuff without destroying its strength or its ability to firmly hold the leg L of the wearer. In comparison to the femoral cuff of the inventor's FIG. 8, FIG. 8a embodiment of U.S. Pat. No. 4,723,539, the bridge 5b is approximately 25-50% wider than the upper bridge thereof, while the lower bridge shown for the femoral cuff of that embodiment has been removed entirely. The inventor has found that by eliminating the lower bridge, the cuff can be made more comfortable for the wearer, since it eliminates a portion which can bind muscles of the upper leg (quadriceps) which bulge outwardly when the leg is in extension, without detracting from the ability of the femoral cuff to firmly hold the thigh of the leg L as the leg is flexed.

Figure 9:
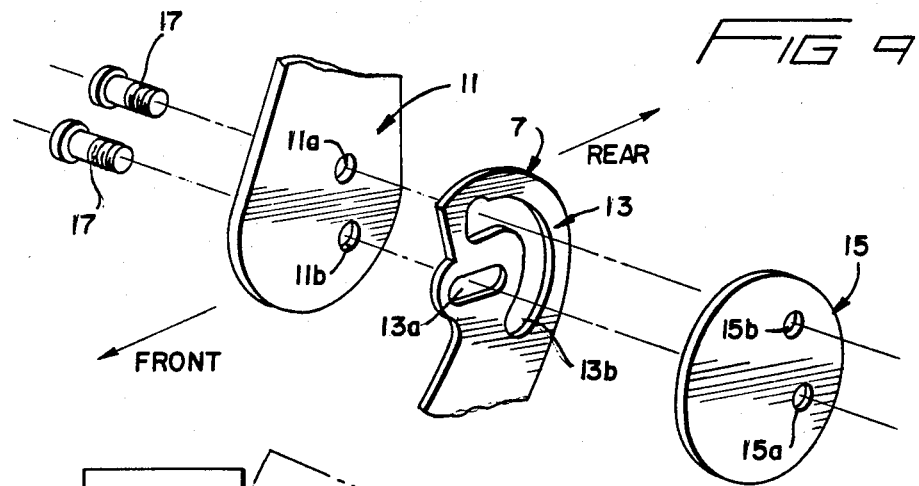
FIG. 9 is an exploded perspective view of the joint mechanism of the orthosis shown in FIG. 1, the motion limiter holes being omitted for purposes of simplicity.

At each of the lateral and medial sides of the orthosis 1, a femoral link 11 is securely joined to a respective wing 5a of the femoral cuff 5 so as to project downwardly therefrom. Similarly, a tibial link 13 is securely joined to the tibial cuff 3, at each of the lateral and medial sides thereof, so as to extend upwardly from the tibial cuff. Any known manner of joining these links to their respective cuffs may be utilized, such as laminating of the links into the cuff or sewing them in, for example. As can be seen from FIG. 1, the femoral and tibial links 11, 13 extend essentially parallel to each other and are disposed so that the outermost ends thereof overlap to enable creation of a mechanical pivot joint 7 at the center of the radius of rotation of the femoral condyle relative to the tibia. As shown in FIG. 9, to complete the joint mechanism, partially threaded screws 17 are passed through unthreaded openings 11a, 11b of the tibial link 11, through slots 13a, 13b of the tibial link 13, and the threaded ends of the screws 17 then fastened within threaded holes 15a, 15b of the cover disk 15, respectively. However, instead of utilizing screws 17, for a more secure, permanent fastening of the components of the joint mechanism 7 together, semitubular rivets (rivets having a solid shaft with a hollowed end portion) may be utilized instead, the hollow ends of the rivets being mushroomed out over the cover disk 15 after passing through holes 15a, 15b, which no longer need be threaded.

As pointed out in the inventor's above-referenced earlier cases, to emulate insofar as is reasonably possible, natural, relative movement of the femur and tibia, a joint mechanism for a knee orthosis should, as the leg is flexed from its extended position, initially produce a limited (approximately 8-9 millimeter) front to rear sliding of the tibia relative to the femur for the first 25 degrees of flexion, and should thereafter, as the knee continues to flex through whatever angle may be traversed, a unicentric pivotal rotation of the tibia relative to the femur. Furthermore, as also pointed out above, it is important that the knee be constrained to move with this natural glide and rotation movement corresponding to that of a normal knee, and to achieve this effect the cam means, in accordance with the present invention, has been found to be most effective in that it facilitates tolerance precision, thereby allowing full control of the forceful action throughout the entire range of motion without undesirable play.

The cam means of the preferred embodiment will now be described in greater detail and is comprised of a pair of camming slots (slots 13a, 13b) which receive and coact with a pair of cam follower means (the shaft of the screws 17 or equivalent rivets passing from holes 11a, 11b to holes 15a, 15b respectively). As can be seen in FIG. 3, the cam slots include a small transversely extending linear slot 13a and a long longitudinally oriented arcuate slot 13b that is in the shape of a circular segment having a slightly upwardly enlarged top end (counterclockwisemost end as shown in FIG. 3). In a manner to be described later on, the transverse slot 13a functions as a means for producing an initial anterior movement of the tibia relative to the femur, while the cam slot 13b governs the subsequent arcuate movement.

Inasmuch as the circular peripheral end portions of the links 11, 13 are matched to the circular periphery of the cover disk 15 slot 13a is centered relative to the vertical bisector of disk 15 as are holes 11a, 15a and the center of the cam follower B, formed by screw 17, when it is situated at the upper end of slot 13b. On the other hand the center of the openings 11a, 15a are transversely displaced from the vertical bisector disk 15 by an amount $O_{A2}$ that is equal to one-half of the allotted travel of the cam follower A within the transverse slot 13a. Similarly, the vertical displacements $O_{A1}$, $O_{B1}$ of the holes 11a, 15a and 11b, 15b, respectively, are matched to the center lines of the slots 13a, 13b and are equal to the radius of curvature r of slot 13b.

Figure 10:
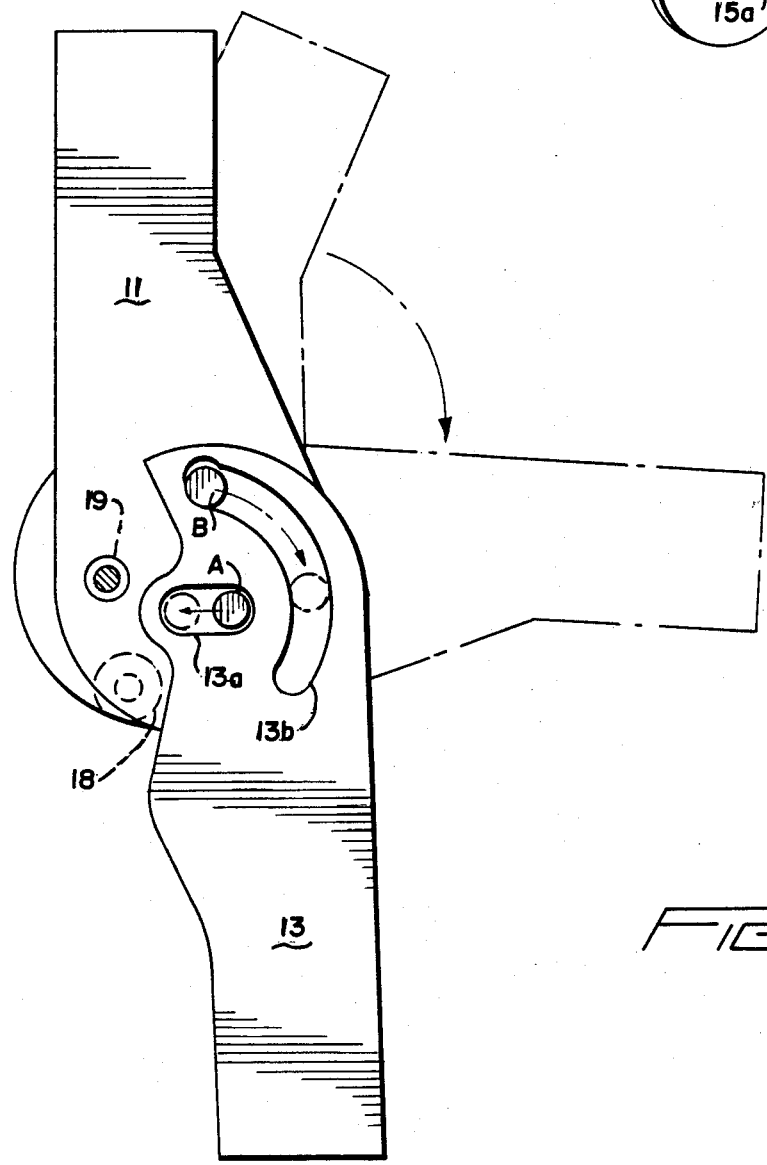
FIG. 10 is a diagrammatic side elevational view of the joint mechanism in accordance with the present invention depicting the relative movement characteristics thereof.

The structure just described produces the following manner of operation, which is illustrated in FIG. 10. In FIG. 10, the relative position of the links 11, 13 and the pivots A, B formed by the screws 17, are depicted as they would be situated in the extended position of the leg shown in FIG. 1. During the first 25 degrees of flexion cam follower A executes a limited rotational movement about cam follower B, causing cam follower A to shift from its solid line position within slot 13a to its phantom line position (shown at the left of slot 13a in FIG. 10). Since the distance between the centers of cam followers A and B is equal to the radius of curvature r, during this initial movement of the cam follower A, cam follower B executes a small vertical movement Y (FIG. 3) into and out of the upwardly enlarged area of slot 13b to compensate for the fact that the vertical distance between the center lines of the slots 13a, 13b will be less than the radius of curvature r for the locus of points between the two end positions of the pivot A within the slot 13a.

Alternatively, instead of upwardly enlarging slot 13b, slot 13a could be given a radius of curvature matched to the pivotal movement of cam follower A about cam follower B. However, the illustrated arrangement is preferred since it has been found to eliminate virtually all play from the joint 7. In this regard, while a considerable clearance is shown between the cam follower A and the walls of slot 13a in FIG. 10, it should be appreciated that such is only for illustration purposes and, in practice, the clearance between the diameter of the shaft of screw 17 and the height of the slot 13a will be precision matched to provide the minimum clearance necessary to ensure free travel of the screw shaft across the slot 13a.

Because the center of the circular segment curvature of the slot 13b is situated at a position that is not reached by the center of the cam follower A until the initial 25 degrees of flexion has occurred until this point is reached it is not possible for the cam follower B to rotate about a pivot created by cam follower A. However, once that position has been reached no further shifting of cam follower A is possible, so that further flexion of the knee will cause the cam follower B to traverse the slot 13b in the direction of the arrows shown in FIG. 10, as pivotal movement of the links 11, 13 now occurs about cam follower A. For example, cam follower B moves from its solid line position to its phantom line position as the femoral link 11 moves from its 25 degree flexure point clockwise to the 90 degrees flexure position (from the first phantom line position, in the direction of the phantom arrow to the second phantom line position) as illustrated.

The maximum degree of flexure that will be permitted is dictated by the angle $\alpha$ representing the angular extent of rotational movement of the tibial link 13 relative to the femoral link 11 about the cam follower A. However, in certain cases, an orthopedic injury or deformity calls for a restriction of the degree to which the knee joint should be permitted to flex in order to ensure that the user cannot injure himself or herself. Thus, in accordance with another aspect of the invention, the joint mechanism 7 is provided with a flexion limiting means which may, optionally, be utilized to limit flexion of the knee to, for example, 60 or 90 degrees of flexion instead of the full range of, for example, 120 degrees of flexion. To this end, the femoral link 11 and the cover disk 15 are provided with a pair of aligned openings 11c, 15c, respectively, those of the disk being tapped to receive the threaded end of a screw 17 that serves as a flexion stop. Additionally, the tibial link 13 is provided with a flexion stop surface 13c. By coordinating the angular orientation β of surface 13c (measured from the initial position of cam follower B) relative to the angular positions of the holes 11c, 15c, these holes and the flexion stop surface can be set so that a pin inserted in one or the other of the holes will abut against flexion stop surface 13c when the desired flexion angle limitation, e.g. 60 or 90 degrees, is reached.

In FIG. 10, a screw 17 is shown inserted into the holes 11c, 15c, corresponding to that required to produce a 90 degree flexion limitation. Additionally, further degrees of control can be achieved without the provision of additional holes 11c, 15c, by disposing washers 18, 19, of different external diameters onto the screws 17, after they have been inserted through the femoral link 11 and prior to threading of the screw 17 into the tapped hole 15c of the cover disk 15. In FIG. 10, a washer 19 is shown mounted on the screw 17 in order to, for example, cause flexion to be limited at 86 degrees instead of 90 degrees. The larger diameter washer 18 could be used instead, to thereby produce, for example, an 8 degree adjustment to the effect of the screw 17, thereby limiting flexion to only 82 degrees. With regard to the angle β for convenience, this angle is selected to be 25 degrees, i.e., is matched to the initial angle of flexion during which relative movement between the femoral and tibial links 11, 13 occurs about cam follower B and to compensate for the fact that the femoral link 11 will have gone through 25 degrees of flexion relative to the tibial link 13 before cam follower B moves.

In a similar fashion, if the wearer's physical condition requires a restriction in the extension of the articulating knee joint, a precise clinical adjustment of the degree of extension permitted may also be obtained. For this purpose, for example, three holes 11d, 15d are provided for use with a screw 17 that serves as an extension stop pin in a manner similar to that described for use as a flexion motion limiter. To coact with a screw 17 disposed in a hole 11d, 15d, the tibial link 13 is provided with an extension stop surface 13d. By setting the angular position of the holes 11d, 15d relative to this stop surface 13d, a screw 17, independently or in combination with a washer 18 or 19, can provide a wide range of extension restriction adjustment; for example, providing limitations at angular points of 4, 8, 12, 16, 20, 24 and 35 degrees of motion. In this regard, it should be recognized that if extension is limited to 25 degrees or more, the joint mechanism 7 will function simply as a single pivot joint, i.e., the sliding movement produced by pivotal movement about cam follower B will be eliminated. Lastly, for convenience purposes, extension stop surface 13d is coaxial with the radius r at the zero point of angle α, i.e., is oriented at an angle α of 180 degrees.

It should be appreciated that such an internal range of motion limiter, such as the flexion and extension stop arrangements described above, when integrated into the joint mechanism 7 of the present invention, not only enables a precise adjustment of the angular range movements obtainable, but does so in a secure manner that is neither cumbersome nor such as to detract from the overall strength of the joint mechanism. Furthermore, the ability to integrate such a motion limiter into the joint mechanism 7 of the present invention is made possible by the reduction of the internal extent of the links and cover disk required for camming slots that is effectuated by the cam means of the present invention. On the other hand, not only does the cam means of the present invention enable the integration of the improved motion limiter described herein, but it also achieves increases the integral strength and tolerance prexision of the joint while retaining a forceful control action having the desired arthrokinematic properties of the inventor's original joints, referenced above.

While a single embodiment has been disclosed in accordance with the present invention it should be understood that the present invention is not limited thereto, but is susceptible of numerous changes and modifications as will be apparent to those skilled in the art, and, therefore, the present invention is not limited to the details shown and described herein but rather all such changes and modifications as are encompassed by the scope of the appended claims are also covered.

I claim:

1. In an appliance for stabilizing a knee joint in sagittal, coronal and transverse planes, having leg grasping means for clasping the appliance to the wearer's leg above and below the knee,
   means defining a mechanical joint at the medial and lateral sides of the knee, each comprising
   a pair of depending opposed femoral links, each said link terminating in an end portion,
   a pair of opposed upwardly extending tibial links terminating in an end portion; each said end portion of said, tibial links being disposed in overlapping relation to a respective said end portion of said femoral links,
   cam means interconnecting each said end portion of said femoral links to a respective said end portion of said tibial links. said cam means being disposed at lateral and medial sides of the knee,
   each said cam means comprising a first and a second cam pin follower and a first and a second camming slot means, each said cam pin follower being fixedly positioned relative to a link of one of said pairs of femoral and tibial links and being relatively displaceable with respect to a link of the other of said pairs of femoral and tibial links within a respective camming slot means, said first and second cam pin followers and first and second camming slot means forming a means for constraining the tibia to slide rearwardly relative to the femur for a predetermined distance during an initial range of flexion of the knee from a straight leg position, by a pivotal movement of one of said femoral and tibial links relative the other of said femoral and tibial links about said second cam follower means, and said first and second cam follower means and said first and second camming slot means forming a means for constraining beyond said initial range of flexion, one of said femoral and tibial links to rotate relative to the other of said femoral and tibial links in a predetermined arcuate path about said first cam follower means.

2. An appliance according to claim 1, wherein said initial range of flexion is about 25°.

3. An appliance according to claim 2, wherein said arcuate path is a circular segment having a center of curvature located at a position corresponding to the location reached by said first cam follower means after relative displacement thereof during said initial range of flexion.

4. An appliance according to claim 1, wherein said arcuate path is a circular segment having a center of curvature located at a position corresponding to the location reached by said first cam follower means after relative displacement thereof during said initial range of flexion.

5. An appliance according to claim 1, wherein said first camming slot means comprises a relatively short, lineal slot and said second camming slot means comprises a relatively long, arcuate slot.

6. An appliance according to claim 5, wherein said first camming slot means extends in a transverse direction relative to a longitudinal extent of said links and said second camming slot means extends in a generally longitudinal direction relative thereto.

7. An appliance according to claim 6, wherein said initial range of flexion is about 25°.

8. An appliance according to claim 7, wherein said arcuate path is a circular segment.

9. An appliance according to claim 5, wherein said arcuate path is a circular segment.

10. An appliance according to claim 1, wherein both of said first and second cam pin followers are carried by the same one of said femoral and tibial links and said first and second camming slots are formed in the same other one of said femoral and tibial links.

11. An appliance according to claim 1, further comprising motion limiter means having adjustable abutment means for limiting the extent to which said mechanical joint is able to permit the leg of a wearer to extend.

12. An appliance according to claim 11, wherein the adjustable abutment means of said motion limiter means comprises stop pin means carried by one of said femoral and tibial links and an extension stop surface formed on the other of said femoral and tibial links, and means for permitting the position of said stop pin means relative to said extension stop surface to be changed.

13. An appliance according to claim 12, wherein said motion limiter means further comprises flexion limiting means for limiting the extent to which said mechanical joint is able to permit the leg of a wearer to flex.

14. An appliance according to claim 13, wherein said flexion limiting means also comprises stop pin means carried by one of said femoral and tibial links and an flexion stop surface formed on the other of said femoral and tibial links, and means for permitting the position of said stop pin means relative to said extension stop surface to be changed.

15. An appliance according to claim 1, further comprising motion limiter means having adjustable abutment means for limiting the extent to which said mechanical joint is able to permit the leg of a wearer to flex.

16. An appliance according to claim 15, wherein the adjustable abutment means of said motion limiter means comprises stop pin means carried by one of said femoral and tibial links and an flexion stop surface formed on the other of said femoral and tibial links, and means for permitting the position of said stop pin means relative to said flexion stop surface to be changed.

17. An appliance according to claim 1, wherein said leg grasping means comprises a femoral cuff and a tibial cuff to which said femoral and tibial links are connected, respectively, and wherein said femoral cuff is n shaped, having a pair of wings for laterally engaging against an upper leg area of the wearer, said wings being connected only at a top portion of a frontal edge thereof by a connecting bridge for preventing binding of the quadriceps of the wearer.

18. In an appliance for stabilizing a knee joint in sagittal, coronal and transverse planes, having leg grasping means for clasping the appliance to the wearer's leg above and below the knee;

means defining a mechanical joint at the medial and lateral sides of the knee, each comprising a pair of depending opposed femoral links, each said link terminating in an end portion;

a pair of opposed upwardly extending tibial links, each said link terminating in an end portion;

a pair of cover disks; and connecting means interconnecting each said end portion of one of said tibial and said femoral links to a respective cover disk via a respective said end portion of the other of said femoral and said tibial links, said connecting means being disposed at each of lateral and medial sides of the knee and being comprised of elements which coact to form a movement control means for constraining the tibia to slide rearwardly relative to the femur for a predetermined distance throughout an initial range of flexion of the knee from a straight leg position and, beyond said initial range of flexion, to rotate relative thereto along a predetermined arcuate patch; and motion limiting means comprised of stop pin means mountable so as to extend between the end portion of said one of said tibial and femoral links and said cover disk, and at least one abutment stop surface formed on an edge of the end portion of the other of said femoral and said tibial links in a patch of movement of said stop pin means, and means for changing the relative angle between said tibial and femoral links at which said stop pin means will abut said abutment stop surface comprising at least one annular washer that is removably mountable on the stop pin means for changing the diameter of a portion of the stop pin means that is disposed between the cover disk and said end portion of the said one of the tibial and femoral links.

19. An appliance according to claim 18, wherein said one of said tibial and said femoral links is the femoral link, and said other of said femoral and tibial links is the tibial link.

20. An appliance according to claim 18, wherein said means for changing comprises a plurality of holes, at differing angular positions relative to abutment stop means, for selective interchangeable mounting of said stop pin means.

* * * * *